US008501458B2

(12) United States Patent (10) Patent No.: US 8,501,458 B2
Strobel et al. (45) Date of Patent: Aug. 6, 2013

(54) SYSTEM AND METHOD OF PRODUCING VOLATILE ORGANIC COMPOUNDS FROM FUNGI

(76) Inventors: Gary A. Strobel, Bozeman, MT (US); Angela R. Tomsheck, Oilmont, MT (US)

( * ) Notice: Subject to any disclaimer, the term of this patent is extended or adjusted under 35 U.S.C. 154(b) by 0 days.

(21) Appl. No.: 13/110,688

(22) Filed: May 18, 2011

(65) Prior Publication Data

US 2011/0287471 A1 Nov. 24, 2011

Related U.S. Application Data

(60) Provisional application No. 61/345,918, filed on May 18, 2010.

(51) Int. Cl.
*C12N 1/00* (2006.01)
(52) U.S. Cl.
USPC ........... 435/254.1; 435/41; 435/171; 435/243
(58) Field of Classification Search
None
See application file for complete search history.

(56) References Cited

U.S. PATENT DOCUMENTS

| 4,275,234 | A | 6/1981 | Baniel et al. |
|---|---|---|---|
| 4,297,109 | A | 10/1981 | Sugito et al. |
| 5,348,872 | A | 9/1994 | Lin et al. |
| 5,510,526 | A | 4/1996 | Baniel et al. |
| 5,641,406 | A | 6/1997 | Sarhaddar et al. |
| 5,831,122 | A | 11/1998 | Eyal |
| 2005/0220769 | A1 | 10/2005 | Strobel et al. |
| 2009/0123977 | A1* | 5/2009 | Mendez et al. ............... 435/91.4 |

FOREIGN PATENT DOCUMENTS

WO WO 93/00440 1/1993

OTHER PUBLICATIONS

Sanchez-Ballesteros et al., Mycologia, 92(5): 967-977 (2000) (Abstract only).*
Azeez, S. (2008). "Fennel. In Chemistry of Spices", pp. 227-241. Edited by Parthasarathy, V.A., Chempakam, B., & Zachariah, T. Cambridge, MA: CAB International.
Barton, A., & Tjandra, J. (1989). "Eucalyptus oil as a cosolvent in water-ethanol-gasoline mixtures." Fuel 68, 11-17.
Bunge, M., et al. (2008). "On-line monitoring of microbial volatile metabolites by proton transfer reaction-mass spectrometry." Appl Environ Microbiol 74, 2179-2186.
Cook, et al, (2007), "*Mentha spicata* essential oils rich in 1,8.cineole and 1,2-epoxy-P-methane derivates from Zakynthos (Ionian Island, W Greece)". The Journal of Essential Oil Research 19, 225-230.
Cosimi, et al., (2009). "Bioactivity and qualitative analysis of some essential oils from Mediterranean plants against stored-product pests: Evaluation of repellency against *Sitophilus zeamais* Matschulsky, *Cryptolestes ferrugineus* (Stephens) and *Tenebrio molitor* (L.)." Journal of Stored Products Research 45, 125-132.
Croteau, et al., (1994). "Biosynthesis of monoterpenes: partial purification, characterization and mechanism of action of 1,8-cineole synthase." Arch-Biochem-Biophys 309, 184-192.
Ezra, et al., (2004a), "New endophytic isolates of *Muscodor albus*, a volatile-antibiotic-producing fungus." Microbiology 150, 4023-4031.
Ezra, et al., (2004b). Proton transfer reaction-mass spectroscopy as a technique to measure volatile emissions of *Muscodor albus*. Plant Science 166, 1471-1477.
Kempler, G.M. (1983). "Production of Flavor Compounds by Microorganisms. III. Terpenenes." B. Production of Monoterpenes by Microorganisms. In Advances in Applied Microbiology, vol. 29, pp. 35-37. Edited by A.I. Laskin. New York, NY: Academic Press, Inc.
Madyastha, K. M. (1984). "Microbial transformations of acyclic monoterpenes." Journal of Chemical Sciences 93, 677-686.
Smith, S.A., et al. (2008) "Bioactive Endophytes Warrant Intensified Exploration and Conservation" PloS 1 Biology Published on-line Aug. 25, 2008, PloS 1 3(8):e3052.
Southwell, et al., (2003), "*Melaleuca teretifolia* chemovars: New Australian sources of citral and 1,8-cineole." Journal of Essential Oil Research 15:339-341.
Strobel, G.A., & Daisy, B. (2003). "Bioprospecting for Microbial Endophytes and Their Natural Products." Microbiology and Molecular Biology Reviews 67, 491-502.
Strobel, et al., (2001). "Volatile antimicrobials from *Muscodor albus*, a novel endophytic fungus." Microbiology 147, 2943-2950.
Strobel, et al., (2008). "The production of myco-diesel hydrocarbons and their derivatives by the endophytic fungus *Gliocladium roseum* (NRRL 50072)." Microbiology 154, 3319-3328.
Tan, R., & Zou, W. (2001). "Endophytes: a rich source of functional metabolites." Nat. Prod. Rep. 18, 448-459.
Thomas, et al., (2000). "Plant sources of aroma chemicals and medicines in India." Chemical Industry Digest (Special Millennium Issue), 104-108.
Weyerstahl, et al., (1993). "Constituents of the Leaf Essential Oil of *Persea indica* (L.) K. Spreng." Flavour and Fragrance Journal 8, 201-207.
Worapong, et al., (2001). "Muscodor albus anam, nov., an endophyte from *Cinnamomun zeylanicum*." Mycotaxon 79, 67-79.
Griffin et al., "Protoplast formation and transformation of *Hypoxylon mammatum*." Abstracts of the 1989 APS Annual Meeting. Phytopathology 1989, 79:1135; p. 1204.
Zhao et al., "Study on the Preparation and Regeneration of Protoplast From Taxol-Producing Fungus *Nodulisporium ylviforme*." 2004, Nature and Science 2(2):52-59.
Johannesson Ecology of *Daldinia* spp. With Special Emphasis on *Daldinia Zoculata*. Doctoral thesis. Swedish University of Agricultural Sciences Uppsala. 2000.

* cited by examiner

*Primary Examiner* — Blaine Lankford, Jr.
*Assistant Examiner* — Thomas J Visone
(74) *Attorney, Agent, or Firm* — Riverside Law LLP

(57) ABSTRACT

An isolated fungus is described. The isolated fungus produces at least one compound selected from the group consisting of 1,8-cineole, 1-methyl-1,4-cyclohexadiene, and (+)-α-methylene-α-fenchocamphorone. A method for producing at least one compound selected from the group consisting of 1,8-cineole, 1-methyl-1,4-cyclohexadiene, and (+)-α-methylene-α-fenchocamphorone is also described. The method includes culturing a fungus on or within a culturing media in a container under conditions sufficient for producing the at least one compound.

12 Claims, 7 Drawing Sheets

1-methyl-1,4-cyclohexadiene    1,8-cineole (+)-.alpha.-methylene-.alpha.-fenchocamphorone

SEQUENCE LISTING

<160> NUMBER OF SEQ ID NOS: 2

<210> SEQ ID NO 1
<211> LENGTH: 19
<212> TYPE: DNA
<213> ORGANISM: Artificial Sequence
<220> FEATURE:
<223> OTHER INFORMATION: Chemically synthesized

<400> SEQUENCE: 1
tccgtaggtg aacctgcgg                                    19

<210> SEQ ID NO 2
<211> LENGTH: 20
<212> TYPE: DNA
<213> ORGANISM: Artificial Sequence
<220> FEATURE:
<223> OTHER INFORMATION: Chemically synthesized

<400> SEQUENCE: 2
tcctccgctt attgatatgc                                   20

SYSTEM AND METHOD OF PRODUCING VOLATILE ORGANIC COMPOUNDS FROM FUNGI

CROSS REFERENCE TO RELATED APPLICATIONS

The present application claims priority from U.S. Provisional Application No. 61/345,918, filed May 18, 2010, the entire disclosure of which is incorporated by reference herein as if set forth herein in its entirety.

STATEMENT REGARDING FEDERALLY SPONSORED RESEARCH OR DEVELOPMENT

This invention was made with government support under CBET-0802666 and EFRI-0937613 awarded by the National Science Foundation (NSF), and under N00244-09-1-0070 awarded by the Department of Defense (Navy). The government has certain rights in the invention.

BACKGROUND OF THE INVENTION

The identification and production of volatile organic compounds (VOCs) continues to be a driving force in the development and expansion of many commercial industries. For example, 1,8-cineole, commonly referred to as eucalyptol, is the pharmaceutically active component of eucalyptus oil, comprising 70-85% of the essential oil. Traditional uses of eucalyptus oil primarily involve non-prescription pharmaceuticals, fragrances and degreasing detergents (Opdyke, 1975, Food and Cosmetics Toxicology 13: 91-112; Hong and Shellock, 1991, American Journal of Physical Medicine and Rehabilitation 70:29-33; Leung, Y. (1980). *Eucalyptus*. New York: Wiley.; Furia, T., & Bellanca, N. (1971). *Fenaroli's Handbook of Flavor Ingredients*. Cleveland, Ohio: Chemical Research Co.; Barton, et al., 1997, Chemistry in Australia 64:4-6). 1,8-Cineole also has potential applications in alternative fuel production as it has been shown to prevent phase separation when used as an additive in ethanol-gasoline fuel blends (Barton and Tjandra, 1989, Fuel 68:11-17), and alternative fuels comprised of a gasoline/eucalyptus oil mixture (with 1,8-cineole as the major fuel component) resulted in an improved octane number and reduced carbon monoxide exhaust (U.S. Pat. No. 4,297,109).

Also, fenchocamphorone is a derivative of fenchol via a fenchene intermediate, both of which are monoterpenes (Croteau, et al., 1988, Journal of Biological Chemistry 263: 15449-15453). Fenchone, also a monoterpene of similar derivations, is a volatile compound that is found as a major constituent of fennel seed oil (Azeez, S. (2008). Fennel. In *Chemistry of Spices*, pp. 227-241. Edited by Parthasarathy, V. A., Chempakam, B., & Zachariah, T. Cambridge, Mass.: CAB International.). Fennel oil is also considered an essential plant oil and is valued for its strong flavor, but is also recognized as an antioxidant, hepatoprotective agent, anticancer agent, and other biological activities have been described for it (Azeez 2008; Cosimi et al., 2009, Journal of Stored Products Research 45:125-132).

Another example is 1,4-cyclohexadiene, which is a highly flammable cycloalkene that yields the natural monoterpene derivative, γ-terpinene, a component associated with many essential oils. 1,4-Cyclohexadiene also readily oxidizes to benzene by a number of different methods (Breton, et al., 2005, Electrochemistry Communications 7:1445-1448; Smith and Gray, 1990, Catalysis Letters 6:195-200; Hepworth et al., 2002, Aromatic Chemistry, pp. 129-134; Brooks, B. T. (1922). The Cyclic Non-benzoid Hydrocarbons: The Cyclohexane Series. In *The Chemistry of Non-benzoid Hydrocarbons and Their Simple Derivatives*, pp. 278-383. Edited by B. T. Brooks. New York, N.Y.: Chemical Catalog Company, Inc.) which gives it multiple applications in industrial chemistry. Benzene is a natural component of crude oil and gasoline and is a widely used chemical in the production of plastics, nylon, and resins, as well as some types of rubbers, detergents, lubricants, dyes, and pesticides (Agency for Toxic Substances and Disease Registry (ATSDR) (2007). *Toxicological Profile for Benzene (Update)*. Atlanta, Ga.: U.S. Department of Public Health and Human Services, Public Health Service).

However, a major limiting factor in widespread industrial applications of these volatile compounds, particularly 1,8-cineole, pertains to its biological source. Currently, this monoterpenoid is produced solely by plants restricted to certain species of *Eucalyptus*, but also including *Rosmarinus officinalis* (Rosemary), and *Thymus valgaris* (Thyme) (Thomas, et al., 2000, Chemical Industry Digest (Special Millennium Issue) pp. 104-108), *Melaleuca teretifolia* (Southwell, et al., 2003, Journal of Essential Oil Research 15:339-341), and *Mentha spicata* (Cook, et al., 2007, The Journal of Essential Oil Research 19:225-230). A novel and more bountiful source for these compounds could significantly advance their industrial application profiles.

Endophytes, microorganisms that reside in the tissues of living plants (Stone et al., Microbial Endophytes, Ed. C. W. Bacon and J. F. White Marcel Decker, Inc, NY, 2000), are relatively unstudied and potential sources of novel natural products for exploitation in medicine, agriculture and industry. It is worthy to note, that of the nearly 300,000 plant species that exist on the earth, each individual plant is host to one or more endophytes. Only a handful of these plants have ever been completely studied relative to their endophytic biology. Consequently, the opportunity to find new and interesting endophytic microorganisms among myriads of plants in different settings, and ecosystems is great. Currently, endophytes are viewed as an outstanding source of bioactive natural products because there are so many of them occupying literally millions of unique biological niches (higher plants) growing in so many unusual environments.

It is well accepted that microorganisms can be a production source of chemical compounds, enzymes and other complexes that have industrial utility. The prospect that endophytes produce novel bioactive products stems from the idea that some endophytes may have coevolved with their respective higher plant, and as a result may produce certain phytochemicals characteristic of their hosts (Strobel and Daisy, 2003, Microbiology and Molecular Biology Reviews 67:491-502; Tan and Zou, 2001, Nat. Prod. Rep. 18:448-459). The enormous diversity generated by the presence of microbial life forms is amplified by their ability to inhabit novel niches, ranging from deep ocean sediments to the earth's thermal pools. Endophytic fungi inhabit one such biological niche and are characterized by their ability to asymptomatically colonize living plant tissues. There are untold numbers of potential novel fungal genera, of which endophytes constitute a significant proportion (Smith, et al., 2008, PloS 1 3(8): e3052). Ecosystems exhibiting the greatest plant diversity also seemingly exhibit the greatest abundance and diversity of microbial endophytes. Ultimately, biological diversity implies chemical diversity as constant chemical innovation is required in such highly competitive ecosystems. Thus, the search for novel endophytic microbes is ongoing, with activity of their natural products encompassing their use as antibiotics, antiviral compounds, anticancer agents, antioxidants, insecticides, antidiabetic agents, and immunosuppressive compounds (Strobel and Daisy, 2003, Microbiology and Molecular Biology Reviews 67:491-502).

One such endophyte is *Hypoxylon* spp., which is a fungal endophyte of *Persea indica*, an evergreen tree native to the Canary Islands, where it grows not in abundance but is found on several islands including Tenerife in the Laurisilva. *Persea* spp. are also native to Central and South America and were later introduced into Southern California (Zentmyer, et al., 1990, California Avocado Society 1990 Yearbook 74:239-242).

Undoubtedly, production of 1,8-cineole, among other volatile organic compounds such as 1-methyl-1,4-cyclohexadiene and (+)-α-methylene-α-fenchocamphorone by a fungal source, would have significant implications for use of such compounds in widespread industrial applications. Therefore, a need exists for the identification and production of volatile organic compounds produced by fungi. The present invention satisfies this need.

SUMMARY OF THE INVENTION

The present invention relates to an isolated fungus that produces at least one compound selected from the group consisting of 1,8-cineole, 1-methyl-1,4-cyclohexadiene, and (+)-α-methylene-α-fenchocamphorone. In one embodiment, the fungus is from the genus *Hypoxylon*. In a further embodiment, the fungus is isolate Co27-5 (deposited as NRRL 50500). In another embodiment, the fungus is isolate C14A (deposited as NRRL 50501). In another embodiment, the fungus is isolate Ti-13 (deposited as NRRL 50502). In another embodiment, the fungus is isolate Ec-38 (deposited as NRRL 50503). In another embodiment, the fungus is from the genus *Nodulosporium*. In another embodiment, the fungus is from the genus *Daldinia*. In another embodiment, the fungus is from the genus *Muscodor*.

The present invention also relates to a method for producing at least one compound selected from the group consisting of 1,8-cineole, 1-methyl-1,4-cyclohexadiene, and (+)-α-methylene-α-fenchocamphorone. The method includes culturing a fungus on or within a culturing media in a container under conditions sufficient for producing the at least one compound. In one embodiment, the method further includes isolating the at least one compound from the culturing media or from vapor in the container. In a further embodiment, the fungus is from the genus *Hypoxylon*, such as one of isolates Co27-5, C14A, Ti-13 or Ec-38. In another embodiment, the fungus is from the genus *Nodulosporium*. In another embodiment, the fungus is from the genus *Daldinia*. In another embodiment, the fungus is from the genus *Muscodor*.

The present invention also relates to a kit for making at least one compound selected from the group consisting of 1,8-cineole, 1-methyl-1,4-cyclohexadiene, and (+)-α-methylene-α-fenchocamphorone. The kit includes at least one fungus and instructions for growing the fungus for production of the at least one compound.

The present invention also relates to an isolated nucleic acid molecule from a fungus encoding a polypeptide involved in the synthesis or production at least one compound selected from the group consisting of 1,8-cineole, 1-methyl-1,4-cyclohexadiene, and (+)-α-methylene-α-fenchocamphorone.

The present invention also relates to a method for generating mutant strains of a fungus with an increased production rate or production amount of at least one compound selected from the group consisting of 1,8-cineole, 1-methyl-1,4-cyclohexadiene, and (+)-α-methylene-α-fenchocamphorone. The method includes the steps of mutating spores of the fungus, culturing the mutated spores, and screening the cultures of mutated spores for enhanced production rate or production amount of at least one compound selected from the group consisting of 1,8-cineole, 1-methyl-1,4-cyclohexadiene, and (+)-α-methylene-α-fenchocamphorone.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 2, comprising

DETAILED DESCRIPTION

Figure 1:
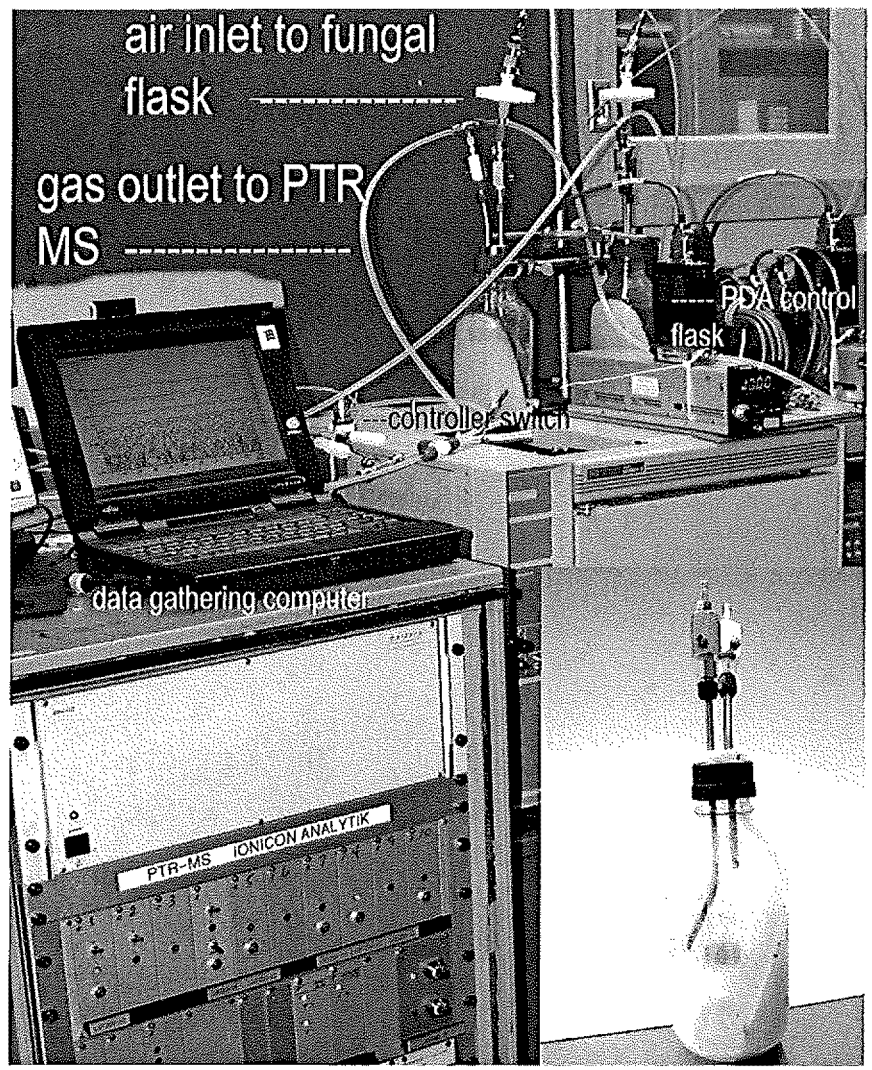
FIG. 1 depicts a PTR-mass spectrometer used to monitor VOC production by *Hypoxylon* sp. The *Hypoxylon* sp. culture produced 100.5 mg dry weight of surface mycelium covering the 121.6 cm$^2$ agar slant at 7 days. Monitoring began 2.5 days after the fungus was inoculated onto the agar surface. The inset shows the details of the hardware used to regulate gas flow into the culture flask. The controller switch continuously changes input of gases from the control bottle (only PDA) to the fungal culture. The computer screen shows the contiuous output of individual ions found in the gas phase.
Figure 2A:
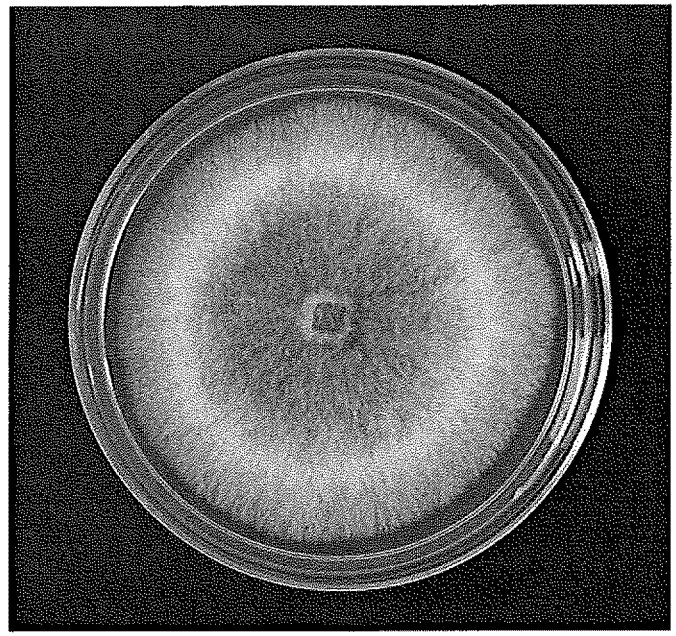
FIGS. 2A and 2B, depicts a 10-day old culture of *Hypoxylon* sp. grown on PDA from both the top side (2A) and bottom side (2B). The darker aspect of the photos represents varying degrees of a greenish-tan coloration.
Figure 2B:
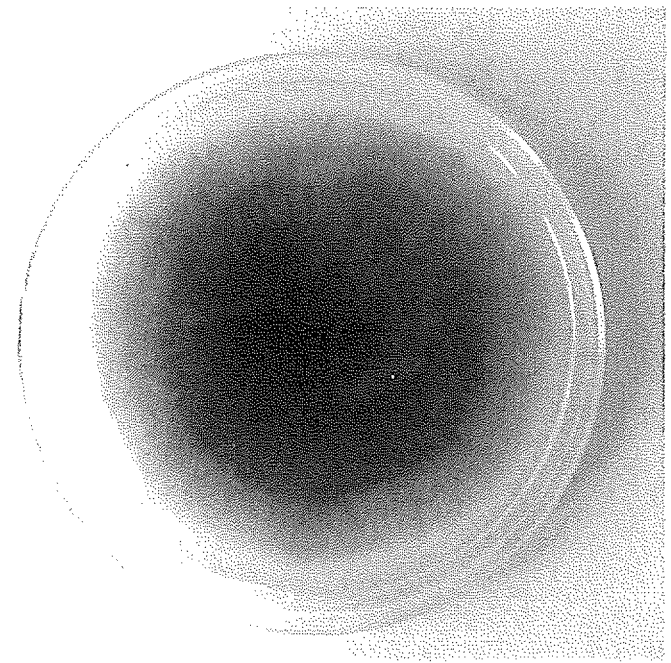
Figure 3:
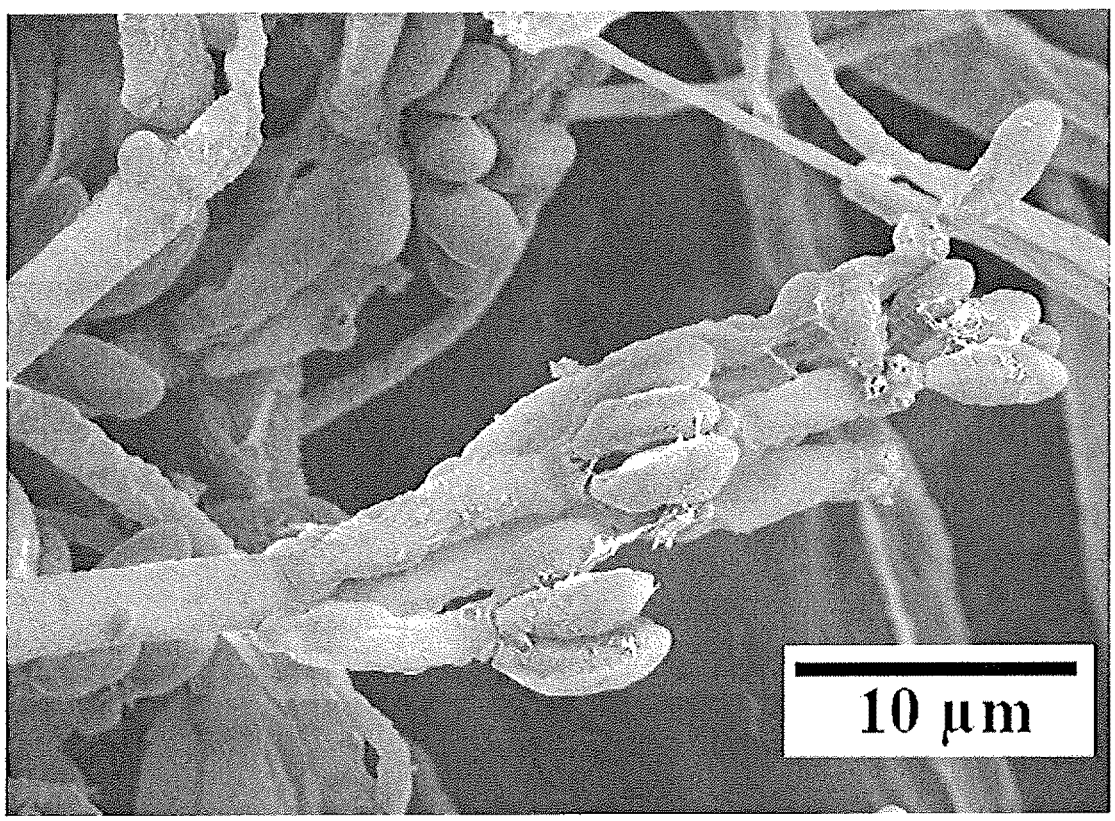
FIG. 3 is an SEM image of a branched conidiophore *Nodulosporium* sp. (I-4) depicting conidia and scars from the budding verticles of the conidiophore.
Figure 4:
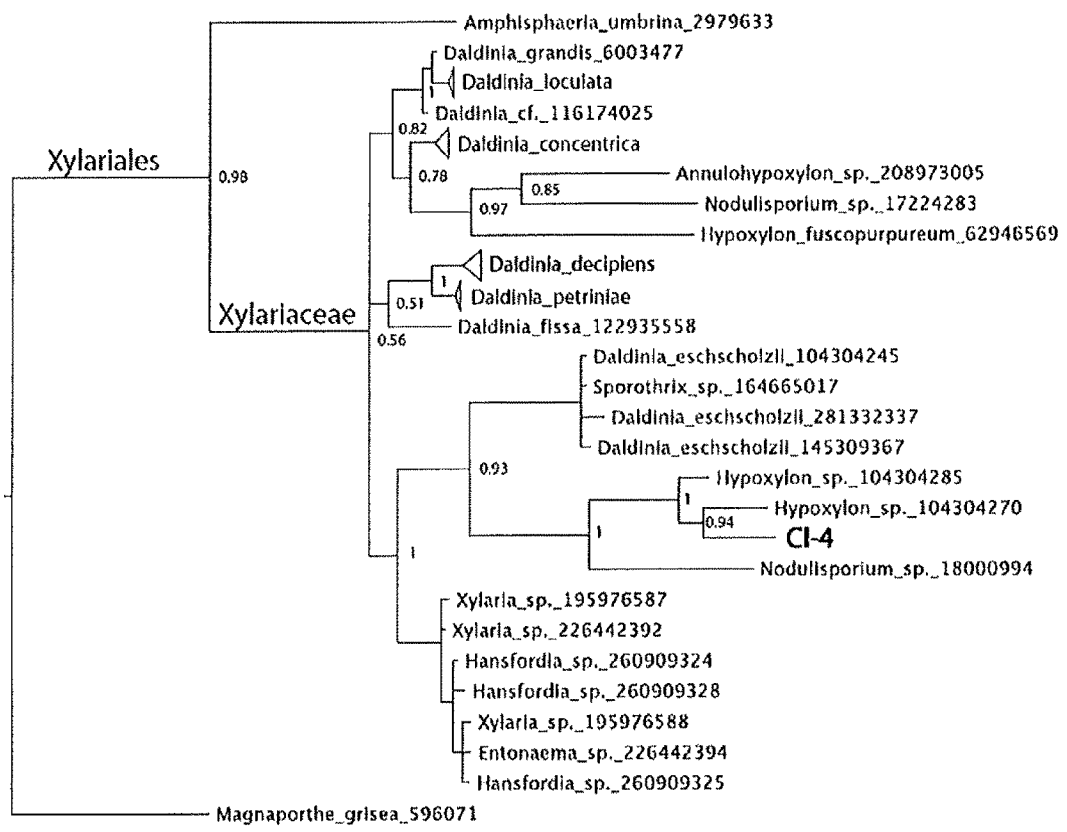
FIG. 4 is chart demonstrating the evolutionary relationships of *Hypoxylon* sp. (CI-4) with 20 other close taxons (BLAST based). The evolutionary history was inferred using the Neighbor-Joining method (Saitou and Nei, 1987, Molecular Biology and Evolution 4:406-425). The optimal tree with the sum of branch length=0.83699359 is shown. All positions containing gaps and missing data were eliminated from the dataset (complete deletion option). There were a total of 307 positions in the final dataset. Phylogenetic analyses were conducted in MEGA4 (Tamura, et al., 2007, Molecular Biology and Evolution 24:1596-1599).

The present invention relates to isolated fungal lines capable of producing an impressive spectrum of volatile organic compounds (VOCs), most notably 1,8-cineole, 1-methyl-1,4-cyclohexadiene, and (+)-α-methylene-α-fenchocamphorone, among many others (see Table 3, below). The present invention also relates to methods of producing such VOCs from fungus, and collecting or recovering the produced VOCs for commercial and/or industrial use.

The present invention is based on the discovery that selected fungi, including numerous *Hypoxylon* spp., produce an impressive spectrum of VOCs, most notably 1,8-cineole, 1-methyl-1,4-cyclohexadiene, and (+)-α-methylene-α-fenchocamphorone. Media containing starch and/or sugar related substrates best supports VOC production by fungus. Direct on-line quantification of VOCs was measured by proton transfer mass spectrometry (PTR-MS) covering a continuous range, with optimum VOC production occurring at 6 days at 145 ppmv with a rate of production of 7.65 ppmv/hr. This demonstrated that 1,8-cineole (a monoterpene) is produced by a microorganism, which represents a novel and important source of this compound. 1,8-cineole is an octane derivative and has potential use as a fuel additive, as do the other VOCs of this organism, listed in Table 3, below. Thus, fungal sourcing of this compound and other VOCs as produced by *Hypoxylon* sp. and other fungi described herein greatly expands their potential applications in medicine, industry, and energy production.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, the term "hydrocarbon" generally refers to a chemical compound that consists of the elements carbon (C) and hydrogen (H). All hydrocarbons consist of a carbon backbone and atoms of hydrogen attached to that backbone. Hydrocarbons are of prime economic importance because they encompass the constituents of the major fossil fuels (coal, petroleum, natural gas, etc.) and biofuels, as well as plastics, waxes, solvents and oils.

The term "fungus" or "fungi" includes a wide variety of nucleated, spore-bearing organisms that are devoid of chlorophyll. Examples of fungi include yeasts, molds, mildews, rusts, and mushrooms.

The term "bacteria" includes any prokaryotic organism that does not have a distinct nucleus.

The term "isolated" means altered or removed from the natural state or biological niche through the actions of a human being.

The term "antibiotic" includes any substance that is able to kill or inhibit a microorganism. Antibiotics may be produced by a microorganism or by a synthetic process or semisynthetic process. The term, therefore, includes a substance that inhibits or kills fungi for example, cycloheximide or nystatin.

The term "culturing" refers to the propagation of organisms on or in solid or liquid media of various kinds.

The term "effective amount" is an amount sufficient to effect beneficial or desired results. An effective amount can be administered in one or more administrations. In terms of treatment and protection, an "effective amount" is that amount sufficient to ameliorate, stabilize, reverse, slow or delay progression of the target infection or disease states.

The term "metabolite" or "volatile" refers to any compound, substance or byproduct of a fermentation of a microorganism that has a biological activity.

The term "mutant" refers to a variant of the parental strain as well as methods for obtaining a mutant or variant in which the desired biological activity is similar to that expressed by the parental strain. The "parent strain" is defined herein as the original fungus (e.g. *Hypoxylon*) strains before mutagenesis. Mutants occur in nature without the intervention of man. They also are obtainable by treatment with or by a variety of methods and compositions understood by those of skill in the art. For example, parental strains may be treated with a chemical such as N-methyl-N'-nitro-N-nitrosoguanidine, ethylmethanesulfone, or by irradiation using gamma, x-ray, or UV-irradiation, or by other means.

The term "variant" refers to a strain having all the identifying characteristics of the strains of fungus and can be identified as having a genome that hybridizes under conditions of high stringency to the genome of the organism. A variant may also be defined as a strain having a genomic sequence that is greater than 85%, more preferably greater than 90% or more preferably greater than 95% sequence identity to the genome of the organism. A polynucleotide or polynucleotide region (or a polypeptide or polypeptide region) has a certain percentage (for example, 80%, 85%, 90%, or 95%) of "sequence identity" to another sequence, which means that, when aligned, that percentage of bases (or amino acids) are the same in comparing the two sequences. This alignment and the percent homology or sequence identity can be determined using publicly available software programs known in the art.

The term "instructional material," as that term is used herein, includes a publication, a recording, a diagram, or any other medium of expression which can be used to communicate the usefulness or procedural steps of the invention in the kit for growing the fungi under optimal conditions for optimal VOC production.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, 6 and any whole and partial increments therebetween. This applies regardless of the breadth of the range.

Further, all numerical designations, e.g., pH, temperature, time, concentration, and molecular weight, including ranges, are approximations which may be varied (+) or (−) by increments of 0.1. It is to be understood, although not always explicitly stated that all numerical designations are preceded by the term "about". It also is to be understood, although not always explicitly stated, that the reagents described herein are merely exemplary and that equivalents of such are well known in the art.

Fungi Suitable for Production of VOCs

A search for endophytes hosted by the evergreen tree *Persea indica* revealed the presence of a *Hypoxylon* sp., as described herein. An examination of this organism revealed that it produces important VOCs including, without limitation, 1,8-cineole; 1-methyl-1,4-cyclohexadiene, and (+)-α-methylene-α-fenchocamphorone (see Table 3, below). These compounds have potential industrial utility, such as fuels or additives as per the VOCs of some other endophytic fungi now known as Mycodiesel™ (Strobel, et al., 2008, Microbiology 154:3319-3328).

In one aspect, the present invention includes an isolated fungus capable of producing at least one VOC. For example, the following fungal isolates of *Hypoxylon*, each being capable of producing at least one VOC, were deposited under the terms of the Budapest Treaty with the ARS Culture Collection (NRRL), 1815 North University Street, Peoria, Ill. 61604-3999 USA, on May 11, 2011 and assigned the corresponding Accession Numbers:

| *Hypoxylon* sp. | NRRL Accession Number |
|---|---|
| Co27-5 | 50500 |
| C14A | 50501 |
| Ti-13 | 50502 |
| Ec-38 | 50503 |

These strains have been deposited under conditions that assure that access to these cultures are readily available to one determined by the Commissioner of Patents and Trademarks to be entitled thereto under 37 C.F.R. §1.14 and 35 U.S.C. §122, and are available as required by foreign patent laws in countries wherein counterparts of the subject application, or its progeny are filed. However, it should be understood that the availability of a deposit does not constitute a license to practice the subject invention in derogation of patent rights granted by governmental action. Based on these deposits, the entire genomes of *Hypoxylon* isolates Co27-5, C14A, Ti-13, Ec-38 or Ni-25 2A are hereby incorporated into and included in this filing.

Figure 5:
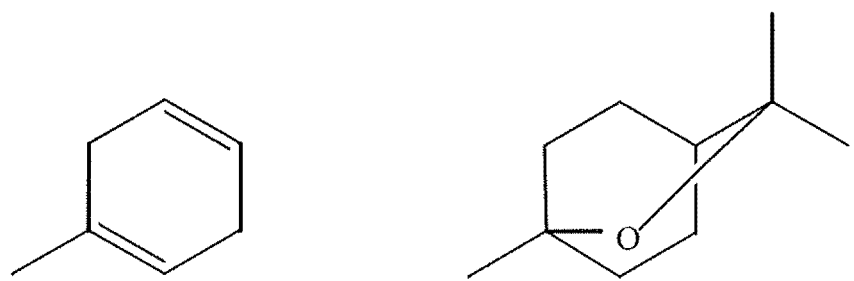
FIG. 5 is a structural depiction of the fungal volatile organic compounds I-methyl-1,4-cyclohexadiene (top left), 1,8-cineole (top right), and (+)-α-methylene-α-fenchocamphorone (bottom).
Figure 5:
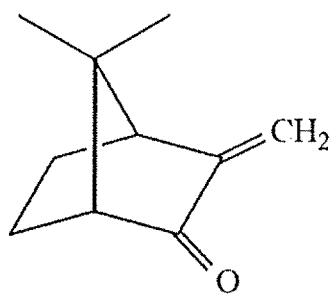

In one embodiment of the present invention, any one of the fungi described herein can produce an impressive spectrum of volatile organic compounds (see Table 3, below) including, without limitation, 1,8-cineole, 1-methyl-1,4-cyclohexadiene, and (+)-α-methylene-α-fenchocamphorone, the structures of which are depicted in FIG. 5. It should be appreciated that the present invention is not limited to production of the aforementioned VOCs by *Hypoxylon*. Rather, the present invention includes production of VOCs, particularly 1,8-cineole, 1-methyl-1,4-cyclohexadiene, and (+)-α-methylene-α-fenchocamphorone, by any fungus, or for that matter, any microorganism. For example, 1,8-cineole can also be produced by an isolated *Muscodor* sp., such as Ni5, and is therefore also contemplated as forming part of the present invention. In another example, the present invention relates to endophytic fungi that produce volatile organic compounds, such as hydrocarbons, from isolates of *Nodulosporium* spp, *Hypoxylon* spp., *Daldinia* spp. and *Muscodor* spp. These compounds produced by the fungus can then be used in a variety of commercial industries, including medicine, energy production, and fuel additives or constituents. This novel, renewable source of hydrocarbons is desirable because it provides a supplement to the existing limited resources of non-renewable hydrocarbons.

Furthermore, it should be appreciated that the disclosed *Hypoxylon* isolates can also be classified as an endophytic *Nodulosporium* sp. or *Daldinia* sp., depending on the fungal identification methodology used. Generally speaking, almost all fungi have a perfect (sexual stage) and an imperfect stage (non sexual), and each is given a name. For example, *Nodulosporium*-like organisms can have the perfect stage of *Hypoxylon* or *Daldinia*. Therefore, as contemplated herein, fungi identified as any one of *Nodulosporium* spp., *Hypoxylon* spp., and *Daldinia* spp. form part of the present invention for the generation of VOCs, as described herein. Further, the fungi of the present invention include all anamorphs and teleomorphs, to the extent such forms exist and are available. For example, the *Hypoxylon* strains Co27-5, C14A, Ti-13 and Ec-38 have *Nodulosporium* sp. as their anamorphic stage. The difference between an anamorph and teleomorph is that one is the asexual state and the other is the sexual state, where the two states exhibit different morphology under certain conditions. In cases where fungi reproduce both sexually and asexually, these fungi may have two names. For example, the teleomorph name describes the fungus when reproducing sexually, while the anamorph name refers to the fungus when reproducing asexually. Also, the holomorph name refers to the "whole fungus", encompassing both reproduction methods. When referring to any one of these names as describing a fungus, all such fungal stages or forms are contemplated and included in the present invention, regardless of whether a different or alternative name may exist. Thus, it should be appreciated that for the aforementioned *Nodulosporium* spp., *Hypoxylon* spp. and *Daldinia* spp., and even *Muscodor* spp., and synonyms thereof, the present invention encompasses both the perfect and imperfect ("anamorph") states, and other taxonomic equivalents, e.g., teleomorphs, regardless of the species name by which they are called. Those skilled in the art will readily recognize the identity of appropriate equivalents.

As will be appreciated by one of skill in the art, microorganisms such *Nodulosporium* spp., *Hypoxylon* spp., *Daldinia* spp. and *Muscodor* spp. can be used in combination with other microbes (e.g. yeasts or other bacteria) for the large scale production of biofuels.

As contemplated herein, the present invention also includes isolated strains of a *Nodulosporium*, *Hypoxylon*, *Daldinia* or *Muscodor*, wherein the isolated fungal strain was serially propagated. When strains are serially propagated, some of the characteristics of the strain may change. Such changes include deletion or suppression of metabolic pathways, an increase in certain metabolic pathways, changes to the chromosome, genes and/or operons (e.g. via mutations or changes in the regulatory factors that control the expression level of said genes or operons). For example, a strain of *Hypoxylon* may have changes in its metabolic characteristic and/or genetic make-up as compared to *Hypoxylon* isolates Co27-5, C14A, Ti-13, Ec-38 or Ni-25 2A. Such changes to the metabolic characteristics and/or genetic make-up may increase and/or decrease the production of the specific compounds listed in Table 3. Methods for isolating mutant cells with a desired characteristic are well known in the art. See, for example, U.S. Pat. No. 5,348,872, which is herein incorporated by reference in its entirety.

The present invention also provides a method for producing volatile organic compounds, such as hydrocarbons. In one embodiment, the method comprises culturing isolates of *Nodulosporium* spp, *Hypoxylon* spp., *Daldinia* spp. and *Muscodor* spp. under conditions sufficient for producing VOCs, and collecting or recovering the produced VOCs. The methods of the present invention also include any combination of procedures and steps used in the culturing of fungi and recovery of at least one VOC, as described hereinthroughout.

Volatile Organic Compounds Produced by Fungi

As stated previously, the present invention relates to endophytic fungi that produce volatile organic compounds, such as the hydrocarbons listed in Table 3, below. Of particular interest is the production of 1,8-cineole, 1-methyl-1,4-cyclohexadiene, and (+)-α-methylene-α-fenchocamphorone, the structures of which are depicted in FIG. 5. Each of these compounds is either itself a monoterpene or is a direct derivative of a monoterpenic compound. Given that monoterpenes are prime constituents of essential plant oils, production of such compounds by an endophytic fungus may lie in support of the idea that as these fungi coevolved with their respective higher plant hosts there was a gene transfer resulting in the production of characteristic host phytochemicals (Strobel and Daisy, 2003, Microbiology and Molecular Biology Reviews 67:491-502). Whether or not this is consistent for this particular endophyte, 1,8-cineole is not known to be a constituent of essential oils collected from leaves of a *Persea indica* plant in California (Weyerstahl, et al., 1993, Flavour and Fragrance Journal 8:201-207). However, this possibility should not be disregarded, given the highly diverse environment of this isolate. The ability of *Hypoxylon* sp, to synthesize monoterpenic compounds typically associated with antimicrobial activity exemplifies the ability for microorganisms to inhabit essential oil producing plants, and their potential role in acquiring the biosynthetic pathways of these compounds should not be overlooked (Table 2).

1,8 Cineole has a broad spectrum of uses, from over-the-counter medical ointment to solvent/degreasers to flavoring/fragrances to alternative fuel. Thus, production of 1,8-cineole by a fungal isolate is significant and greatly expands its potential for a broad spectrum of industrial applications. For example, previous studies have shown prevention of phase separation when 1,8-cineole is used as an additive in ethanol-gasoline fuel blends (Barton and Tjandra, 1989, Fuel 68:11-17), and alternative fuels comprised of a gasoline/eucalyptus oil mixture, with 1,8-cineole as the major fuel component, resulted in an improved octane number and reduced carbon monoxide exhaust (Sugito, K., & Takeda, S. (1981). U.S. Pat. No. 4,297,109).

In certain embodiments, the VOCs may be hydrocarbons, and may be useful for the production of biofuels, plastics, plasticizers, antibiotics, rubber, fuel additives, and/or adhesives. As will be appreciated by one of skill in the art, hydrocarbons can also be used for electrical power generation and heating. The chemical, petrochemical, plastics and rubber industries are also dependent upon hydrocarbons as raw materials for their products. As used herein, the term "biofuel" refers generally to any fuel that derives from biomass, i.e. recently living organisms or their metabolic byproducts, such as manure from cows, or a hydrocarbon produced by fungi. A biofuel may be further defined as a fuel derived from a metabolic product of a living organism.

While the production of other monoterpenes like citronellol, geraniol, linalool, nerol, and α-terpinol by microorganisms such as *Ceratocystis* spp., *Trametes odorata*, *Phellinus* spp., and *Kluyveromyces lactis* (Kempler, G. M. (1983). Production of Flavor Compounds by Microorganisms. III. Terpenenes. B. Production of Monoterpenes by Microorganisms. In *Advances in Applied Microbiology*, Vol 29, pp. 35-37. Edited by A. I. Laskin. New York, N.Y.: Academic Press, Inc.) has been demonstrated, the present invention represents the first time that 1,8-cineole and the other volatile products listed in Table 3 can be produced by endophytic fungi. Prior to this, the only known biological source of 1,8-cineole was from plant tissue. Production of VOCs from fungi represents a far superior commercial production model than from plants.

Biosynthesis of 1,8-cineole involves its conversion from geranyl pyrophosphate by 1,8-cineole cyclase (cineole synthase), whose activity is inhibited by cysteine- and histidine-directed reagents but protected by substrate-metal ion complexes, with the ether oxygen atom of this oxygen-containing terpene being solely derived from water (Croteau, et al., 1994, Arch-Biochem-Biophys 309:184-192). In comparison, fenchocamphorone is also converted from geranyl pyrophosphate and proceeds through the pathway as the intermediate (−)-(3R)-linalyl pyrophosphate via (−)-endo-fenchol cyclase (synthase) which subsequently cyclizes in the presence of the (4R)-α-terpinyl and (1R,5R)-pinyl cations to form (−)-endo-Fenchol which can further oxidize to α/β-fenchocamphorone (Croteau, et al., 1988, Journal of Biological Chemistry 263: 15449-15453). An understanding of these individual pathways and their derivation from a common pathway involving production of geranyl pyrophosphate from mevalonate (MVA pathway) agrees with the idea that *Hypoxylon* sp. may be conditioned for biosynthesis of monoterpenes and subsequent manipulation of these pathways could lead to their optimum production on a mass commerical scale.

Growth Substrates and Culturing of Fungi for Production of VOCs

It should be appreciated that any substrate suitable for promoting fungal growth may be used in the production of VOCs, including without limitation any of the components listed in Table 4, in any ratios and combinations, as would be understood by those skilled in the art. As contemplated herein, high starch substrates promote optimal VOC production, as demonstrated by substrate utilization assays containing high amounts of starch as a carbohydrate source (Table 4). In certain embodiments, cellulose may also be a suitable substrate. Given the enormous volumes of accumulating cellulitic biomass and the utilization of foodstuff grains in alcohol (fuel) production, microorganisms that utilize cellulose for the production of VOCs are quite attractive.

For example, in some embodiments, the culture media for culturing fungi may include substrates comprising oatmeal, barley, or potato agar bases. The culture media may also be a PDA medium, a cellulose medium, and may include starch, glucose, or any combination of components listed in Table 4. Further, the selected fungal strain may be grown in a medium containing any combination of inorganic salts, organic nitrogen sources, such as peptones, defatted cotton seed flour, corn steep liquor, or yeast extract and carbon source. Examples of carbon source may include, but is not limited to, glucose, lactose, sucrose, cellulose or other carbohydrates. Further still, it should be appreciated that the present invention should not be limited by the type or amount of growth media used, and should include use of any media suitable for cultivating fungi as would be understood by those skilled in the art. In other embodiments, these conditions can also include culturing fungi in the absence of oxygen (anaerobic conditions) or in reduced oxygen conditions (e.g., microaerophilic conditions).

Generally speaking, the isolated fungi of the present invention can be cultured using standard methods as would be understood by those skilled in the art. Alternatively the fungal cultures can be cultured on a large scale for commercial use, by using conventional fermentation techniques. In this context fermentation is used broadly to refer to any controlled fungal culturing conditions. Prior to large scale growth an inoculum of said growth culture is generally cultured. In certain embodiments, the fungi can be cultured in a bioreactor vessel for a scaled up production of VOCs. Any conventional bioreactor vessel can be used as the vessel for the purpose of this invention. For example, the vessel may be made of materials such as stainless steel, glass, plastic, and/or ceramics, and may have a volume of from about 100 ml to 10,000 L or larger. The bioreactor vessel may be connected to a series of storage flasks that contain nutrient solutions and solutions for maintaining and controlling various parameters of the cultivation and VOC recovery process. Depending on the particular needs of the fermentation, there may be separate storage flasks for individual supply of substrates to the vessel, which substrates serve as the carbon, nitrogen or mineral source for the living cells in the vessel.

Further, several methods can be used to grow the various fungal isolates for use in the invention. Fed Batch culture is a variation on ordinary batch culture and involves the addition of a nutrient feed to the batch. Cells are cultured in a medium in a fixed volume. Before the maximum cell concentration is reached, specific supplementary nutrients are added to the culture. The volume of the feed is minimal compared to the volume of the culture. Fed batch culture typically proceeds in a substantially fixed volume, for a fixed duration, and with a single harvest either when the cells have died or at an earlier, predetermined point.

In a continuous culture, the cells are initially grown in a fixed volume of medium. To avoid the onset of the decline phase, fresh medium is pumped into the bioreactor before maximum cell concentration is reached. The spent media, containing a proportion of the cells, is continuously removed from the bioreactor to maintain a constant volume. The process also removes the desired product, which can be continuously harvested, and provides a continuous supply of nutrients, which allows the cells to be maintained in an exponentially growing state. Theoretically, the process can be operated indefinitely. Continuous culture is characterized by a continuous increase in culture volume, an increase and dilution of the desired product, and continuous maintenance of an exponentially growing culture.

Perfusion culture is similar to continuous culture except that, when the medium is pumped out of the reactor, cells are not removed. As with a continuous culture, perfusion culture is an increasing-volume system with continuous harvest that theoretically can continue indefinitely.

Recovery of VOCs

Once produced by the selected fungi isolate, several methods can be used to isolate the VOCs listed in Table 3 from the culture media or from vapor in a growth chamber. For example, common separation techniques can be used to remove the cells from the broth or agar, and common isolation procedures, such as (without limitation) extraction, distillation, and carbocolumn trap procedures, can be used to obtain VOCs from the cell-free broth or agar. See, for example, U.S. Pat. Nos. 4,275,234, 5,510,526; 5,641,406, and 5,831,122, and International Patent Application Number WO 93/00440, each of which is hereby incorporated by reference in its entirety.

Fractional distillation and/or absorption chromatography are also non-limiting examples of methods to extract the desired product produced by fungal isolates of the present invention. Fractional distillation is the separation of a mixture into its component parts, or fractions, such as in separating chemical compounds by their boiling point by heating them to a temperature at which several fractions of the compound will evaporate. Absorption chromatography is a physical separation method in which the components of a mixture are separated by differences in their distribution between two phases, one of which is stationary (stationary phase) while the other (the mobile phase) moves through it in a definite direction. The substances must interact with the stationary phase to be retained and separated by it.

Gas chromatography is a well known technique for fractionating and determining the relative amounts of various components in a sample containing a mixture of compounds of differing volatilities. For example, the sample is vaporized and the entire resulting quantity of gases is passed through an analytical chromatography column. Chromatographic processes such as gas chromatography can rapidly determine the volatiles content of a multicomponent sample, such as would be produced by the fungal isolates of the present invention.

In some instances, Pressure Swing Adsorption (PSA) may be used to separate some gas species from a mixture of gases under pressure according to the species' molecular characteristics and affinity for an adsorbent material. It operates at near-ambient temperatures and so differs from cryogenic distillation techniques of gas separation. Special adsorptive materials (e.g., zeolites) are used as a molecular sieve, preferentially adsorbing the target gas species at high pressure. The process then swings to low pressure to desorb the adsorbent material.

Mutant and/or Engineered Fungi for Enhanced Production of VOCs

The present invention also includes mutant or engineered fungi that ultimately increase the production yield of at least one VOC, or the speed at which the mutant or engineered fungi can produce at least one VOC. Mutant or engineered fungi are obtainable by treatment of fungi with or by a variety of methods and compositions understood by those of skill in the art. For example, parental strains may be treated with a chemical such as N-methyl-N'-nitro-N-nitrosoguanidine, ethylmethanesulfone, or by irradiation using gamma, x-ray, or UV-irradiation, or by other means.

For example, as contemplated herein, the present invention also includes identifying and cloning genes that encode for production of at least one VOC from the genomes of each fungi described herein. In one embodiment, the *Hypoxylon* genome is probed for the gene or genes (e.g. an operon) that encode the synthetic pathways that produce a VOC from Table 3, such as 1,8-cineole, 1-methyl-1,4-cyclohexadiene, and (+)-α-methylene-α-fenchocamphorone. Thus, the present invention encompasses an isolated nucleic acid molecule from fungi encoding a polypeptide involved in the synthesis or production of at least one VOC. In another embodiment, an isolated nucleic acid molecule is at least 65%, at least 70%, at least 75%, at least 80%, at least 85%, at least 90%, at least 95%, at least 96%, at least 97%, at least 98%, or at least 99% identical to said isolated nucleic acid molecule from any one of the fungi isolates described herein. In another embodiment, a polypeptide sequence is at least 65%, at least 70%, at least 75%, at least 80%, at least 85%, at least 90%, at least 95%, at least 96%, at least 97%, at least 98%, or at least 99% identical to a polypeptide from any one of the fungi isolates described herein.

Methods to clone and/or probe genomes for synthetic pathways may include creating cDNA and/or genomic libraries, and screening the libraries for genes that produce the VOC synthetic pathways. Thus, the present invention comprises a DNA and/or chromosomal library of any one of the fungi isolates described herein. In one embodiment, the library is cloned into a vector that can replicate in a prokaryotic cell and/or eukaryotic cell. In another embodiment, the eukaryotic cell is a fungal cell. In another embodiment, the library is a lambda phage, Yeast Artificial Chromosome, Bacterial Artificial Chromosome, and/or cDNA. In another embodiment, the library is screened for production of VOCs from Table 3, such as 1,8-cineole, 1-methyl-1,4-cyclohexadiene, and (+)-α-methylene-α-fenchocamphorone.

Another method for determining the gene, genes and/or operon(s) that encode for the production of VOCs include mutagenizing the genome of any one of the fungi described herein and looking for an increase, addition, reduction or removal of a specific VOC. This can be accomplished via chemical and/or transposon mutagenesis. Once a gene, genes and/or operon(s) is identified, said gene, genes or operon(s) can be cloned and/or isolated. Thus, one embodiment of the invention comprises an isolated nucleic acid of any one of the fungi described herein, wherein the nucleic acid molecule is cloned into a vector. In another embodiment, said nucleic acid molecule encodes for a gene, genes, or operon(s) that encode for proteins involved in the production of VOCs of Table 3. In another embodiment, the vector autonomously replicates or integrates into the host's chromosome. In another embodiment, said vector is transformed or transfected into a heterologous cell. In another embodiment, said heterologous cell is selected from the group consisting of a prokaryotic or eukaryotic cell.

The present invention also encompasses variants and fragments of polynucleotides and/or proteins of any one of the fungi described herein that produce or are part of the pathway (s) that produce VOCs. The variants may contain alterations in the nucleotide and/or amino acid sequences of the constituent proteins. The term "variant" with respect to a polypeptide refers to an amino acid sequence that is altered by one or more amino acids with respect to a reference sequence. The variant can have "conservative" changes, or "nonconservative" changes, e.g., analogous minor variations can also include amino acid deletions or insertions, or both. In addition, the nucleotides can be sequenced to ensure that the correct coding regions were cloned and do not contain any unwanted mutations.

Nucleic acid molecules encoding one or more biosynthetic enzyme or protein, and orthologs and homologs of these sequences, may be incorporated into transformation or expression vectors of any one of the fungi described herein. As used herein, the term "vector" refers generally to a nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art. A transformed cell is a cell into which has been introduced a nucleic acid molecule by molecular biology techniques. The term encompasses all techniques by which a nucleic acid molecule might be introduced into such a cell, including transfection with viral vectors, transformation with plasmid vectors, and introduction of naked DNA by electroporation, lipofection, and particle gun acceleration.

Once the gene(s) and/or operon(s) of any one of the fungi described herein have been identified, cloned, transformed, transfected or infected into a heterologous organism (or new organism from a synthetic genome), the heterologous organism can be grown to produce and purify the desired VOCs, including those listed in Table 3.

Thus, the present invention also includes a method for generating mutant strains of a fungus with an increased production rate or production amount of at least one compound, such as 1,8-cineole, 1-methyl-1,4-cyclohexadiene, and (+)-α-methylene-α-fenchocamphorone, or any other compound listed in Table 3, below. The method includes the steps of mutating spores of the fungus, culturing the mutated spores, and screening the cultures of mutated spores for enhanced production rate or production amount of at least one compound selected from the group consisting of 1,8-cineole, 1-methyl-1,4-cyclohexadiene, and (+)-α-methylene-α-fenchocamphorone.

Kits

The present invention also provides for a kit comprising one or more containers filled with one or more of the ingredients of the compositions of the invention. The present invention provides kits that can be used in any of the methods described herein. In one embodiment, a kit comprises at least one *Nodulosporium* sp., *Hypoxylon* sp., *Daldinia* sp. or *Muscodor* sp., in one or more containers. The organism can be supplied frozen in media, freeze dried and/or as spores. The kit may also include instructional material for growing the fungi under optimal conditions for optimal VOC production. The methods in the instructions may include specific bioreactor volumes, purification schemes, optimal temperature, pH, and/or other conditions. The kit may also include the growth media. The media contained in the containers of these kits may be present as a ready-to-use formulation, or as a more concentrated formulation. In addition, the media can be supplied in dry powder. Thus, a kit can comprise a dry power of the media of the invention and a liquid to suspend the media. The liquid may be water or buffers known in the art. Filters for sterilization of the media may also be provided.

EXPERIMENTAL EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way any portion of the disclosure.

Fungal Isolation and Storage

Endophytic fungal culture, CI-4, was obtained as an endophyte from an evergreen tree (*Persea indica*), native to the Canary Islands. One small limb was excised from *Persea indica* found growing on the island of Tenerife, Spain, at N-28° 32' 23"; W-16° 16' 16". Other plant species sampled from this same island included *Acacia* sp., *Pinus canariensis, Prunus lusitanica* and *Rhamnus glandifolia*, none of which fostered recovery of CI-4. Isolation procedures followed a previously described protocol (Worapong, et al., 2001, *Cinnamonum zeylanicum*. Mycotaxon 79:67-79; Ezra, et al., 2004, Microbiology 150:4023-4031). Briefly, external tissues were thoroughly exposed to 70% ethanol prior to excision of internal tissues which were cultured on standard Petri dishes of water agar and glycerol arginine medium (GAM). Endophytic fungi growing from the plant tissues were then picked and re-cultured on potato dextrose agar (PDA). It is also notable that CI-4 grows readily in the presence of the VOCs of *M. albus*, which should facilitate its ready isolation from other plant sources (Strobel, et al., 2001, Microbiology 147:2943-2950). The fungus was stored by placing small plugs of PDA supporting mycelial growth in 15% glycerol at −70° C. An alternative storage method was also utilized in which the fungus colonized sterile barley seed, which was subsequently air dried and then stored at −70° C.

Scanning Electron Microscopy

Scanning electron microscopy (SEM) was performed on sterile carnation leaves colonized with CI-4, according to the following protocol outlined by Ezra (Ezra, et al., 2004, Microbiology 150:4023-4031). The fungus was grown on PDA, or gamma irradiated carnation leaves for several weeks and then was processed for SEM. The samples were slowly dehydrated in ethanol and then critically point dried, coated with gold and examined with an FEI XL30 scanning electron microscope (SEM) FEG with high vacuum mode using an Everhart-Thornley detector.

Fungal DNA Isolation and Acquisition of ITS-5.8S rDNA Phylogenetics

The fungus was grown on PD broth for 7 days, after which the mycelium was harvested and the genomic DNA extracted using DNeasy Plant and Fungi Mini Kit (Qiagen), according to the manufacturer's directions. The internal transcribed spacer (ITS) regions of the fungus were amplified using PCR with the universal ITS primers ITS I (5' TCC GTA GGT GAA CCT GCG G 3') (SEQ ID NO:1) and ITS4 (5' TCC TCC GCT TAT TGA TAT GC 3') (SEQ ID NO:2). All other procedures were carried out as previously described by Ezra. The DNA was sequenced and submitted to GenBank. Sequences obtained in this study were compared to the GenBank database using the BLAST software. A phylogenetic tree was assembled using MEGA4 (Tamura, et al., 2007, Molecular Biology and Evolution 24:1596-1599) and the Neighbor-Joining method (Saitou and Nei, 1987, Molecular Biology and Evolution 4:406-425) with positions containing gaps and missing data eliminated from the dataset (complete deletion option).

Bioassay Tests for *Hypoxylon* sp. VOCs Against Pathogens

The VOCs produced by CI-4 were tested for inhibitory antimicrobial activity against selected pathogenic fungi and bacteria according to a bioassay test system previously described for analysis of VOCs produced by *Muscodor albus* (Strobel, et al., 2001, Microbiology 147:2943-2950). Optimum production of volatile bioactive compounds was determined by exposing test organisms to cultures of varying ages. Inhibitory activities of the VOCs produced by CI-4 after 3-7 days were compared and maximum inhibition observed would suggest the highest concentration of bioactive VOCs. Subsequent bioassay tests were conducted on a wider range of test organisms at the appropriate point at which CI-4 produced maximal amounts of bioactive VOCs.

The assays were conducted by removing a 2.5 cm wide strip of agar from the mid-portion of a standard Petri plate of PDA, creating two isolated halves of agar. The fungus (CI-4) was inoculated onto one half-moon agar piece and incubated at 23° C. for six days to allow for optimum production of volatile compounds. Test pathogens were inoculated onto the half-moon section of agar opposite the half-moon section inoculated with CI-4. The plate was then wrapped with a single piece of Parafilm and incubated at 23° C. for 24 hours. Growth of yeast and bacteria was then qualitatively assessed based on microbial density of a streak inoculum, while growth of filamentous fungi was quantitatively assessed based on multiple measurements of growth extending from the edge of the inoculum plugs comparable to corresponding controls as described by Strobel (Strobel, et al., 2001, Microbiology 147:2943-2950). Ultimately, viability of each test pathogen for which growth was not observed was evaluated after three days of exposure to CI-4 VOCs by transfer of the original exposed inoculum plug or streak onto a fresh plate of PDA. Viability was then determined via observation of growth within three days (Strobel, et al., 2001, Microbiology 147:2943-2950). All tests were conducted in triplicate.

Media Selection for Preferred Substrate Utilization Assay for VOC Production

A variety of selected media was used to determine a combination of substrates that best facilitated VOC production by CI-4. A single plug taken from an actively growing culture of CI-4 on PDA was used to inoculate each agar based medium. Preliminary quantification of 1,8 cineole was estimated by a human olfactory method since this compound is readily sensed by smell. Independent ratings given on a 7 day old cultures grown at 22° C., that had been sealed with parafilm, by seven different observers on two separate occasions. The rating system was 1 (low to none) up to 5 (maximum production). The evaluations were averaged and the standard deviations calculated.

The amount of fungal mycelial growth was assessed by scraping it directly from the surface of the agar surface, drying, and weighing. The following media were tested: (A) yeast extract 0.1 g $l^{-1}$ plus salts; (B) peptone 0.1 g $l^{-1}$ plus salts; (C) cellulose 25 g $l^{-1}$ plus salts and yeast extract 0.1 g $l^{-1}$; (D) cellulose 25 g $l^{-1}$ plus salts and peptone 0.1 g $l^{-1}$; (E) starch 25 g $l^{-1}$ plus salts and yeast extract 0.1 g $l^{-1}$; (F) starch 25 g $l^{-1}$ plus salts and peptone 0.1 g $l^{-1}$; (G) glucose 25 g $l^{-1}$ plus salts and yeast extract 0.1 g $l^{-1}$; (H) glucose 25 g $l^{-1}$ plus salts and peptone 0.1 g $l^{-1}$; (I) cellobiose 25 g $l^{-1}$ plus salts and yeast extract 0.1 g $l^{-1}$; (J) cellobiose 25 g $l^{-1}$ plus salts and peptone 0.1 g $l^{-1}$; (K) glycerol 25 ml $l^{-1}$ plus salts and yeast extract 0.1 g $l^{-1}$; (L) glycerol 25 ml $l^{-1}$ plus salts and peptone 0.1 g $l^{-1}$; (M) instant mashed potatoes 25 g $l^{-1}$ plus salts and yeast extract 0.1 g $l^{-1}$ (MP); (N) potato dextrose (Difco) (PDA); and (O) oatmeal agar (Difco). The salts and agar concentration used in each medium followed the recipe of the M1-D medium previously outlined by Pinkerton & Strobel (Pinkerton and Strobel, 1976, Proc Natl Acad Sci USA 73:4007-4011). Each assay was performed in duplicate and the data were analysed to obtain mean mass/rate values and standard deviations.

Qualitative Analyses of CI-4 Volatiles

Analysis of gases in the air space above cultures of CI-4 grown for eight days at 23° C. on PDA were conducted according to the following protocol as described by Strobel (Strobel, et al., 2001, Microbiology 147:2943-2950). First, a baked "Solid Phase Micro Extraction" syringe (Supelco) consisting of 50/30 divinylbenzene/carboxen on polydimethylsiloxane on a Stable Flex fibre was placed through a small hole drilled in the side of the Petri plated and exposed to the vapour phase for only 5 min due to the high concentration of fungal VOCs. The syringe was then inserted into the splitless injection port of a Hewlett Packard 6890 gas chromatograph containing a 30 m×0.25 mm I.D. ZB Wax capillary column with a film thickness of 0.50 μm. The column was temperature programmed as follows: 30° C. for 2 min increased to 220° C. at 5° C. $\min^{-1}$. The carrier gas was ultra high purity helium, and the initial column head pressure was 50 kPa. Prior to trapping the volatiles, the fiber was conditioned at 240° C. for 20 min under a flow of helium gas. A 30 sec injection time was used to introduce the sample fiber into the GC. The gas chromatograph was interfaced to a Hewlett Packard 5973 mass selective detector (mass spectrometer) operating at unit resolution. The MS was scanned at a rate of 2.5 scans per second over a mass range of 35-360 amu. Data acquisition and data processing were performed on the Hewlett Packard ChemStation software system. Tentative identification of the compounds produced by CI-4 was made via library comparison using the NIST database, and all chemical compounds described in this report use the NIST data base chemical terminology. Final confirmatory identification was made for any compounds with available authentic standards obtained from Sigma/Aldrich by comparing the GC/MS data of the standards, including 1-8-cineole and 1-methyl-1,4-cyclohexadiene, with GC/MS data of fungal products. The GC/MS tests were conducted several times under different exposure times of the fibre to fungal gases with the 5 min. exposure being the optimum given the large volume of VOCs being made by the fungus.

Quantification of Fungal Volatiles

PTR-MS was used to quantify production of fungal volatiles on a continuous monitoring basis beginning with a 2.5 day old culture growing on a 300 ml slant of PDA in a 1 L bottle at 20±2° C. The bottle possessed an O-ring sealed cap that had been modified to possess both inlet and outlet tubes with 10 std cc/min of purified compressed air (Ezra, et al., 2004, Plant Science 166:1471-1477)(FIG. 1). Monitoring of all ions in produced in the spectrum was done for 7.5 days and the concentration of VOCs was estimated (Ezra, et al., 2004, Plant Science 166:1471-1477; Bunge, et al., 2008, Appl Environ Microbiol 74: 2179-2186; Strobel, et al., 2008, Microbiology 154:3319-3328). Air-space analysis of the cultured and uninoculated samples was done by passing a small flow of air (medical-grade compressed air) through the culture bottles and then diluted with air of the same quality (FIG. 1). The sample lines were constructed entirely from PFA Teflon tubing and fittings. A $\frac{1}{20}$-$\frac{1}{10}$ dilution kept the measurements within the linear dynamic range of the instrument and prevented water from condensing in the sample lines, Mass spectral scans were acquired from 20 to 220 Da.

It is to be recognized that the PTR-MS instrument ionizes organic molecules in the gas phase through their reaction with $H_3O^+$, forming mostly protonated molecules ($MH^+$, where M is the neutral organic molecule) which can then be detected by a standard quadrupole mass spectrometer. This process can be run on real air samples with or without dilution, since the primary constituents of air (nitrogen, oxygen, argon and carbon dioxide) have a proton affinity less than water and thus are not ionized. Most organic molecules (excepting alkanes) have a proton affinity greater than water and are therefore ionized and detected. A further advantage of PTR-MS is that from the known or calculated quantities, the reaction time, the amount of $H_3O^+$ present, and the theoretical reaction rate constant for the proton transfer reaction, the absolute concentration of constituents in a sample can be quantified (Lindinger, et al., 1998, Int J Mass Spectrom Ion Process 173:191-241). Finally, an enormous advantage of PTR-MS is that it can be run in real time and continuously produce data on the concentrations of specific ions of interest.

Concentrations derived from the PTR-MS measurements were calculated using equations derived from reaction kinetics and assume that a reaction rate coefficient to $2 \times 10^{-9}$ ml s$^{-1}$ is appropriate for all compounds (Lindinger, et al., 1998, Int J Mass Spectrom Ion Process 173:191-241; Ezra, et al., 2004, Plant Science 166:1471-1477). This method provides a simple means by which the measured ion intensity at any mass can be expressed as an equivalent concentration. In the event that a particular ion can be ascribed to a single compound, then the concentration of that specific compound can be determined using the same procedure as above followed by correction for dilution and any product ion fragmentation. The product ion distribution is determined from mixtures prepared from pure standards.

Example 1

Biological Activities of the VOCs of *Hypoxylon* sp.

The degree of susceptibility of the assay test organisms was dependent upon the age of the *Hypoxylon* sp. culture to which they were exposed for 24 hr (Table 1).

TABLE 1

Progressive (time course) bioassay showing susceptibility of selected fungal pathogens to *Hypoxylon* sp. VOCs as a function of *Hypoxylon* sp. culture age with a 24 hr exposure to the fungal VOCs. The percentages reported are relative to growth of the test organism on a PDA plate minus *Hypoxylon* sp.

| Test Organism | 3 days | 4 days | 5 days | 6 days | 7 days |
|---|---|---|---|---|---|
| *Phytophthora palmivora* | −16.6% ± 7.8 | 11.1% ± 0.0 | 88.8% ± 0.0 | 100.0% ± 0.0 | 100.0% ± 0.0 |
| *Geotrichium candidum* | 12.5% ± 0.0 | 6.2% ± 8.8 | 25.0% ± 0.0 | 31.2% ± 8.8 | 25.0% ± 17.6 |
| *Rhizoctonia solani* | 75.0% ± 35.3 | 75.0% ± 35.3 | 37.5% ± 53.0 | 87.5% ± 17.6 | 100.0% ± 0.0 |
| *Sclerotinia sclerotiorum* | 28.5% ± 0.0 | 67.8% ± 15.1 | 100.0% ± 0.0 | 100.0% ± 0.0 | 100.0% ± 0.0 |
| *Aspergillus fumigatus* | 10.0% ± 14.1 | 40.0% ± 0.0 | 50.0% ± 14.1 | 100.0% ± 0.0 | 75.0% ± 35.3 |
| *Pythium ultimum* | −3.4% ± 4.9 | 43.0% ± 14.8 | 58.1% ± 6.5 | 97.6% ± 3.2 | 100.0% ± 0.0 |
| *Fusarium solani* | 31.2% ± 0.0 | 15.6% ± 4.4 | 31.2% ± 8.8 | 56.2% ± 17.6 | 43.7% ± 8.8 |
| *Phytophthora cinnamomi* | 6.2% ± 44.1 | 50.0% ± 35.3 | 75.0% ± 0.0 | 100.0% ± 0.0 | 100.0% ± 0.0 |
| *Trichoderma viridae* | 16.6% ± 16.8 | 4.7% ± 6.7 | 19.0% ± 6.73 | 23.8% ± 0.0 | 4.7% ± 0.0 |
| *Cercospora beticola* | 41.6% ± 11.7 | 50.0% ± 0.0 | 75.0% ± 35.36 | 100.0% ± 0.0 | 100.0% ± 0.0 |

A progressive (time course) assay using ten different fungal pathogens was designed to determine the time point at which maximum sensitivity of the test organisms occurred which may also relate to the maximum point of VOC production by the fungus. Inhibitory activity of VOCs produced after three, four, five, six, and seven days was compared and maximum inhibition, suggesting the highest concentration of volatile bioactive substances, occurred at six days with eight of the ten test organisms exhibiting maximum inhibition at this time point. The most sensitive test organisms to the VOCs of *Hypoxylon* sp. were *Phytophthora* spp., *Sclerotinia sclerotiorum*, *Aspergillus fumigatus*, and *Cercospora beticola* (Table 1).

An expanded bioassay test involving 16 plant associated fungi revealed varying degrees of response when evaluated via a bioassay Petri plate test system (Strobel, et al., 2001, Microbiology 147:2943-2950). The organisms showed minimal to complete inhibition with a three day exposure to fungal VOCs from a six day old culture of *Hypoxylon* sp., while there was no inhibition of various yeasts and bacteria (Table 2).

TABLE 2

Effects of the VOCs of a 6 day old culture of *Hypoxylon* sp. on various fungi. Inhibition values were calculated as a percentage of growth inhibition as compared to an untreated control test organism at a 3 day exposure. Tests were conducted in triplicate and results varied as indicated by standard deviations. All organisms were viable after exposure to fungal VOCs.

| Test Organism | Percent Inhibition | D or A |
|---|---|---|
| *Sclerotinia sclerotiorum\** | 90.4% ± 16.5 | A |
| *Fusarium solani* | 63.0% ± 5.6 | A |
| *Mycosphaerella fijiensis* | 50.0% ± 57.7 | A |
| *Pythium ultimum\** | 78.2% ± 14.3 | A |
| *Verticillium dahliae* | 80.0% ± 34.6 | A |

TABLE 2-continued

Effects of the VOCs of a 6 day old culture of *Hypoxylon* sp. on various fungi. Inhibition values were calculated as a percentage of growth inhibition as compared to an untreated control test organism at a 3 day exposure. Tests were conducted in triplicate and results varied as indicated by standard deviations. All organisms were viable after exposure to fungal VOCs.

| Test Organism | Percent Inhibition | D or A |
|---|---|---|
| *Aspergillus fumigatus** | 43.0% ± 16.8 | A |
| *Phytophthora palmivora** | 70.0% ± 38.3 | A |
| *Ceratocystis ulmi* | 42.8% ± 32.0 | A |
| *Botrytis cinerea* | 100.0% ± 0.0 | A |
| *Colletotrichum lagenarium* | 36.1% ± 12.7 | A |
| *Geotrichium candidum** | 27.0% ± 6.7 | A |
| *Rhizoctonia solani** | 66.6% ± 57.7 | A |
| *Phytophthora cinnamomi** | 100.0% ± 0.0 | A |
| *Trichoderma viridae** | 50.0% ± 4.7 | A |
| *Cercospora* beticola* | 100.0% 0.0 | A |
| *Muscodor albus* | 58.3% ± 11.7 | A |

*Denotes organism was also used in the progressive bioassay test system.
D = Dead and A = Alive All organisms, including those exhibiting complete inhibition in the presence of fungal VOCs were viable upon re-culturing on PDA. The most sensitive fungi were *Phytophthora* spp., *Cercospora beticola*, *Sclerotinia sclerotionan*, and *Botrytis cinerea* (Table 2).

Example 2

Composition of Volatiles Produced by *Hypoxylon* sp.

Several GC/MS analyses were conducted on the VOCs produced by an eight day old culture of *Hypoxylon* sp. Controls consisting of uninoculated PDA Petri plates were used to subtract compounds contributed by the medium. Preliminary identification of fungal VOCs was determined by comparison of unknown volatiles with MS data of reference compounds listed in the NIST database. It is to be noted that the bulk of the VOCs could not be conclusively identified. However, for those VOCs which could be identified, authentic standards were used to confirm the identification of possible compounds and included 1,8-cineole and 1-methyl-1,4-cyclohexadiene. In addition, other compounds were tentatively identified on the basis of the % quality of the match to the NIST data base with an arbitrary cut off at 60% quality match. The most abundant compound, as based upon total integrated peak areas of the GC elution profile, was tentatively identified as (+)-α-methylene-α-fenchocamphorone, a monoterpene (Table 3) (FIG. 5).

TABLE 3

A GC/MS air-space analysis of the volatile compounds produced by *Hypoxylon* sp. after eight days incubation at 23° C. on PDA using a SPME fiber. Compounds present in a control PDA Petri plate have been subtracted from the data. Unknown compounds represent those with a quality % value less than 60.

| Retention Time (min) | Relative Area | Possible Compound | Mol. Mass (Da) | Quality |
|---|---|---|---|---|
| 4.53 | 7.3 | *1,4-Cyclohexadiene, 1-methyl- | 94 | 91 |
| 9.01 | 7.6 | *1,8-Cineole | 154 | 96 |
| 13.99 | 58.1 | Cyclohexane, 1,2,4-tris(methylene)- (or isomer) | 120 | 83 |
| 14.22 | 4.6 | 8-anti-methylbicyclo(3.2.1)octa-2,6-diene (or isomer) | 120 | 83 |
| 14.28 | 2.0 | 8-anti-methylbicyclo(3.2.1)octa-2,6-diene (or isomer) | 120 | 87 |

TABLE 3-continued

A GC/MS air-space analysis of the volatile compounds produced by *Hypoxylon* sp. after eight days incubation at 23° C. on PDA using a SPME fiber. Compounds present in a control PDA Petri plate have been subtracted from the data. Unknown compounds represent those with a quality % value less than 60.

| Retention Time (min) | Relative Area | Possible Compound | Mol. Mass (Da) | Quality |
|---|---|---|---|---|
| 14.33 | 3.4 | 1,2,4-Tris(methylene)-cyclohexane (or isomer) | 120 | 81 |
| 21.89 | 1.4 | 6-Aza-1,2,3,3a-tetrahydropyrrolo-[1,2-a]quinoxalin-4 | 189 | 83 |
| 23.13 | 2.5 | Unknown | 136 | |
| 25.21 | 5.9 | Unknown | 114 | |
| 26.11 | 2.3 | 5-ethyl-4,4,5-trimethyl-2-cyclopenten-1-one | 152 | 62 |
| 27.67 | 10.9 | Unknown | 110 | |
| 29.6 | 206.7 | ?(+)-α-methylene-α-fenchocamphorone | 150 | 62 |
| 29.71 | 111.5 | 7-Oxatetracyclo[4.1.0.0(2,4).0(3,5)]-heptane | 94 | 76 |
| 29.76 | 35.5 | Unknown | 94 | |
| 29.79 | 47.8 | Unknown | 92 | |
| 29.95 | 9.5 | Unknown | 108 | |
| 30.2 | 5.5 | Unknown | 144 | |
| 30.35 | 4.0 | Unknown | 150 | |
| 30.42 | 4.4 | Unknown | 66 | |
| 30.55 | 7.2 | Unknown | 138 | |
| 30.7 | 1.3 | Unknown | 103 | |
| 30.72 | 2.5 | Unknown | 150 | |
| 30.77 | 1.9 | 1H-inden-1-one, 2,3,3a,4,7,7a-hexahydro-7a-methyl-, | 150 | 68 |
| 30.88 | 2.6 | 2,4,6-Trimethyl-1,3-benzenediamine | 150 | 72 |
| 30.97 | 3.6 | Unknown | 150 | |
| 31.07 | 4.9 | Unknown | 150 | |
| 31.3 | 55.3 | ?(+)-α-methylene-α-fenchocamphorone | 150 | 78 |
| 31.43 | 1.9 | Unknown | 150 | |
| 32.53 | 1.5 | Unknown | 236 | |

*Denotes that the retention time and MS spectrum closely matched or were identical to an authentic standard compound. Those compounds without a designated footnote have a mass spectrum that most closely matched the appropriate compound in the NIST database. The unknowns had a Quality ranking of less than 60%.
?Denotes that a question remain as to the actual identity of the compound listed, the correct elution time of the actual product remains uncertain-the peaks could represent isomers of (+)-α-methylene-α-fenchocamphorone.

Figure 6:
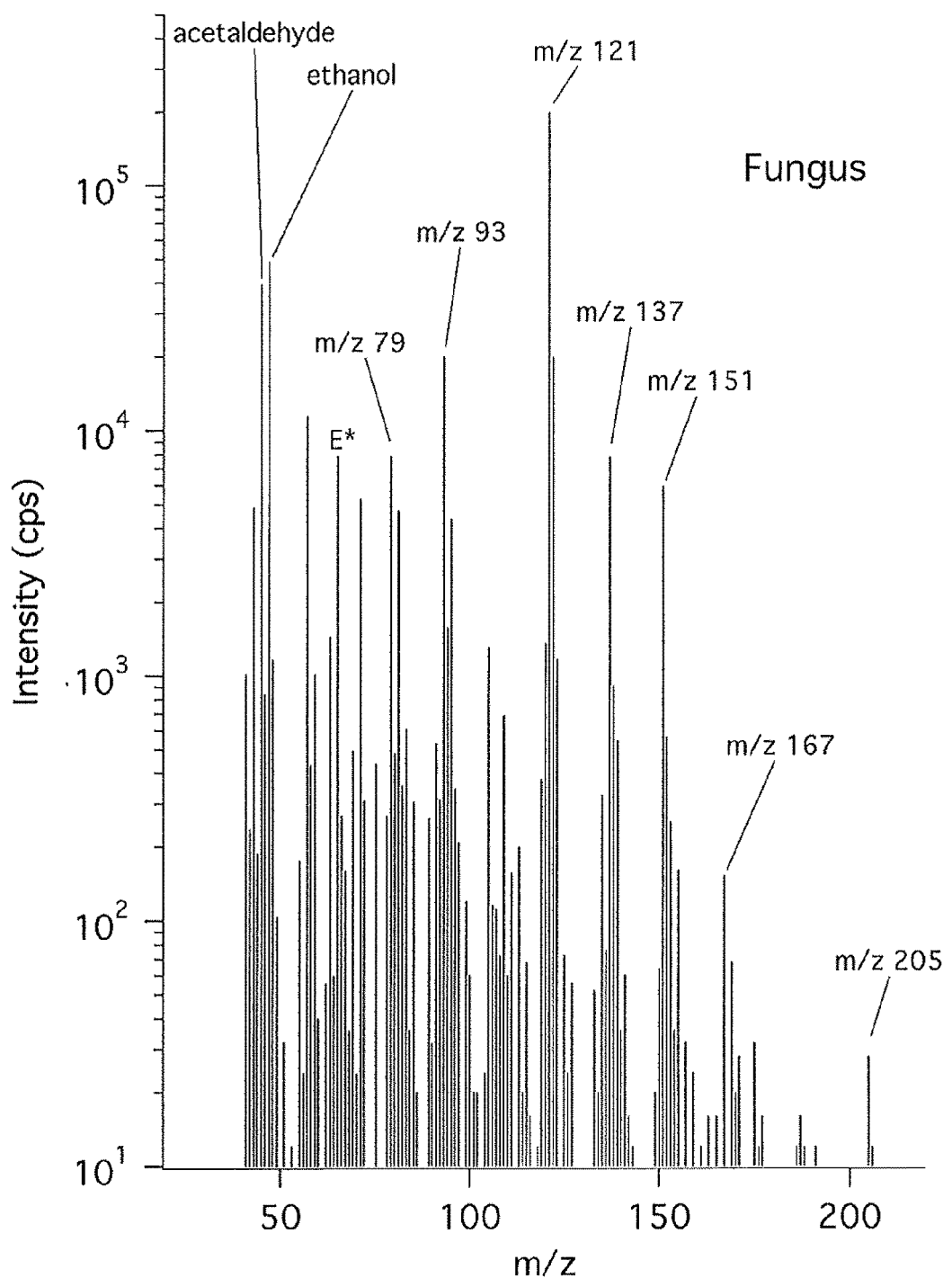
FIG. 6 is a PTR mass spectrum of the head space of a 5-day old culture of *Hypoxylon* sp.

However, at least two peaks appeared designated as this monoterpenoid and these have tentatively been assigned as isomers or relatives of fenchocamphorone since an authentic standard for this compound was not available. A second monoterpene detected in smaller quantities was identified as 1,8-cineole by its NIST data base match, its similarity to the authentic compound, the appearance of peaks at 81, 137 155 in the PTR mass spectrum (identical to its authentic standard), and its characteristic eucalyptus odor all of which are consistent with 1,8-cineole (Table 3; FIGS. 5, 6). The fungus also produced a third compound often considered a derivative of the monoterpene group, 1-methyl-1,4-cyclohexadiene (FIGS. 5, 6). Many other compounds appeared in the GC/MS analysis including cyclohexane, 1,2,4-tris(methylene)-(or isomer), and 8-anti-methylbicyclo(3.2.1)octa-2,6-diene (or isomer) which are probably the chief contributors in the PTR mass spectrum of the 121 peak (M plus H+) (Table 3)(FIG. 6). Other unidentified compounds, many in lesser amounts, were also seen in the VOCs of this fungus on each GC/MS analysis (Table 3). It is to be noted that the results of the GC/MS are at times inconsistent with the PTR-MS and this is due to the fact that the SPME fiber lacks universal adsorption efficiency and likewise the PTR-MS lacks the ability to discern protonated molecular species from other ion fragments. One of the notable discrepancies is the total lack, on repeated analyses, of the SPME fibre to trap the high amounts of ethanol and acetaldehyde that are present in the VOC mix as detected by PTR-MS (Table 3, FIGS. 6, 7). On the other hand, there are many examples in which the data sets of the two MS techniques are compatible, i.e. data for the compound with a MW of 120 and the 1,8 cineole spectra (Table 3 and FIG. 6).

The production of two, possibly three or more monoterpenes/monoterpene derivatives may suggest that the endophyte possesses the enzymatic machinery specialized for the biosynthesis of monoterpenic compounds that are usually associated with higher plants. Monoterpenes are naturally formed products generally associated as common constituents of essential oils and often contribute to antimicrobial activity (Madyastha, 1984, Journal of Chemical Sciences 93:677-686). Biosynthetic pathways leading to the production of such monoterpenes by *Hypoxylon* sp. may suggest possible insight as to its ability to grow in the presence of a highly biologically active fungus, *M. albus*. The comprehensive spectrum of antimicrobial activity exhibited by *M. albus* is yet to be matched by a VOC producing fungus (Strobel, et al., 2001, Microbiology 147:2943-2950). The ability to withstand its own monoterpenic antimicrobials may or may not be linked to its ability to withstand the potent volatile antimicrobials produced by *M. albus*.

Example 3

Substrate Facilitation of VOC Production on Selected Media

There were higher concentrations, in general, of volatile compounds, as detected by an olfactory method when *Hypoxylon* sp. was grown on media enriched with yeast extract over peptone as a source for amino acids (exception seen only in combination with starch). Media containing starch, glucose, and cellobiose as a source of carbohydrates, including PDA, oatmeal agar, and MP, also facilitated higher concentrations of detectable volatile compounds by olfactory methods.

Olfactory qualitative analyses were supported by quantitative measures of surface mycelial mat dry weight on each media type. Surface mycelial mass calculations were conducted following the qualitative analyses and yielded similar substrate preferences. While mass calculations seemed to be dependent first on amino acid sources and second on carbohydrate sources, olfactory ratings seemed to be most dependent on carbohydrate sources. The analyses were both run in duplicate and standard deviations were calculated (Table 4).

TABLE 4

Substrate facilitation of volatile production on different media showing qualitative olfactory observations based on independent ratings 1 to 5 (5 being optimum), and the dry weight of the surface mycelial mat.

| Media | Surface Mass (mg) | Olfactory Rating |
|---|---|---|
| (A.) Yeast | 2.5 ± 0.7 | 1.1 ± 0.4 |
| (B.) Peptone | 1.0 ± 0.0 | 1.3 ± 0.7 |
| (C.) Yeast + Cellulose | 1.5 ± 0.7 | 1.1 ± 0.4 |
| (D.) Peptone + Cellulose | 1.0 ± 0.0 | 1.0 ± 0.0 |
| (E.) Yeast + Starch | 26.5 ± 6.4 | 4.1 ± 1.3 |
| (F.) Peptone + Starch | 30.5 ± 3.5 | 4.1 ± 1.1 |
| (G.) Yeast + Glucose | 22.5 ± 0.7 | 4.0 ± 1.1 |
| (H.) Peptone + Glucose | 11.0 ± 4.2 | 3.4 ± 0.7 |
| (I.) Yeast + Cellobiose | 19.0 ± 1.4 | 3.1 ± 1.2 |
| (J.) Peptone + Cellobiose | 7.5 ± 0.7 | 2.8 ± 0.7 |
| (K.) Yeast + Glycerol | 3.5 ± 0.7 | 2.1 ± 1.2 |
| (L.) Peptone + Glycerol | 1.0 ± 0.0 | 1.5 ± 0.5 |
| (M.) MP | 50.0 ± 2.8 | 4.8 ± 0.5 |

TABLE 4-continued

Substrate facilitation of volatile production on different media showing qualitative olfactory observations based on independent ratings 1 to 5 (5 being optimum), and the dry weight of the surface mycelial mat.

| Media | Surface Mass (mg) | Olfactory Rating |
|---|---|---|
| (N.) PDA | 33.0 ± 4.2 | 5.0 ± 0.0 |
| (O.) Oatmeal | 29.0 ± 2.8 | 5.0 ± 0.0 |

Example 4

Quantification of the VOCs of *Hypoxylon* sp.

Figure 7:
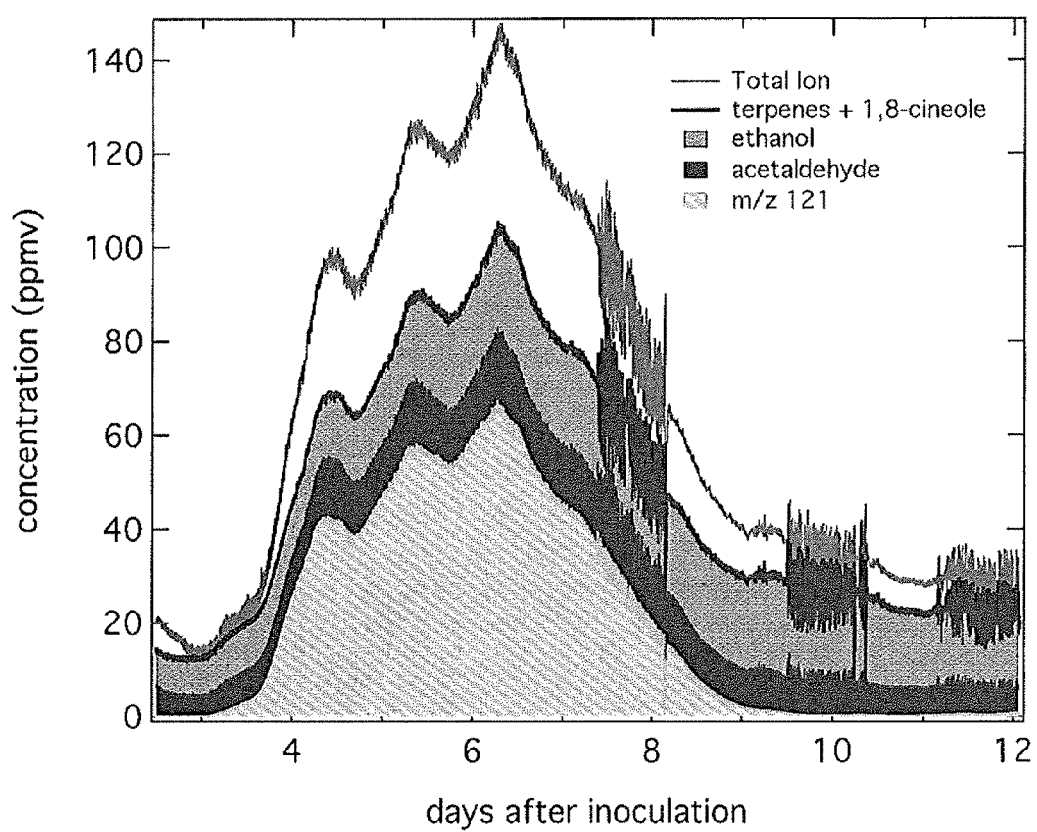
FIG. 7 is a graph of the production of individual compounds in the VOCs of *Hypoxylon* sp. as a function of time as measured and calculated from PTR mass spectral data. The m/z at 121 is likely the series of protonated cyclic alkanes/alkenes whose mass is 120 (See Table 3 herein). The terpenes including 1,8 cineole were calculated from contributions of compounds yielding masses 81, 137 and 155. All calculations are minus the PDA background control flask.

In order to quantify the concentration of volatile products being produced by *Hypoxylon* sp. continuously in the air space over in a 1 L bottle with a 300 ml slant of PDA, a direct method involving PTR-MS was used (FIG. 1). All ions in the PTR spectrum were monitored on a continuous basis and they ranged from mass 41-205 (FIG. 6). The maximum ion output was detected at ca. 6 days of incubation, which is consistent with the sensitivity of the assay organisms to the VOCs of *Hypoxylon* sp. (FIG. 7)(Table 1). Total maximum production of fungal VOCs was a 145 ppmv on day 6 and at a calculated rate of 7.65 ppmv/hr (FIG. 7). It seems that the overall VOC output of this fungus is substantial when compared to the output of other gas producing fungi (Ezra, et al., 2004a, Microbiology 150:4023-4031; Strobel, et al., 2008, Microbiology 154:3319-3328). The chief components of the gas mixture were compounds whose PTR mass spectra were consistent with ethanol, acetaldehyde, and a mass 121 which most likely represents protonated forms of unsaturated compounds whose mass is 120 (Table 3). Ions consistent with 1,8 cineole and other terpenoids producing masses at 81, 137 and 155 also allowed for an estimate of its concentration over the time course of the experiment and they peak at day 5.5-6 (FIG. 7). However, a direct estimate of 1,8 cineole production, based on mass 155, in the flask is ca. 800 ppbv at day 6 which is about 0.5% of the total fungal VOCs.

In summary, six day old cultures of *Hypoxylon* sp. displayed maximal VOC-antimicrobial activity against *Bonytis cinerea, Phytophthora cinnamomi, Cercospora beticola*, and *Sclerotinia sclerotiorum*, suggesting that the VOCs may play some role in the biology of the fungus and its survival in its host plant. Media containing starch- or sugar related substrates best supported VOC production by the fungus, Direct on-line quantification of VOCs was measured by proton transfer mass spectrometry (PTR-MS) covering a continuous range with optimum VOC production occurred at 6 days at 145 ppmv with a rate of production of 7.65 ppmv/hr. This demonstrates that 1,8-cineole (a monoterpene) is produced by a microorganism, which represents a novel and important source of this compound. This monoterpene is an octane derivative and has potential use as a fuel additive as do the other VOCs of this organism. Thus, fungal sourcing of this compound and other VOCs as produced by *Hypoxylon* sp. greatly expands their potential applications in medicine, industry, and energy production.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention, The appended claims are intended to be construed to include all such embodiments and equivalent variations.

What is claimed:

1. An isolated fungus, wherein the fungus is an isolate selected from the group consisting of Co27-5 (deposited as NRRL 50500); CI-4 (deposited as NRRL 50501); Ti-13 (deposited as NRRL 50502); and Ec-38 (deposited as NRRL 50503), and wherein the fungus produces at least one compound selected from the group consisting of 1,8-cineole; 1-methyl-1,4-cyclohexadiene; and (+)-α-methylene-α-fenchocamphorone.

2. The isolated fungus of claim 1, wherein the fungus is serially propagated.

3. The isolated fungus of claim 1, wherein the fungus is grown on or in a high-starch substrate.

4. The isolated fungus of claim 1, wherein the fungus is grown in a liquid medium.

5. The isolated fungus of claim 1, wherein the fungus is grown on a solid medium.

6. A method for producing at least one compound selected from the group consisting of 1,8-cineole; 1-methyl-1,4-cyclohexadiene; and (+)-α-methylene-α-fenchocamphorone, said method comprising culturing a fungus selected from the group consisting of Co27-5 (deposited as NRRL 50500); CI-4 (deposited as NRRL 50501); Ti-13 (deposited as NRRL 50502); and Ec-38 (deposited as NRRL 50503), and wherein the fungus produces at least one compound selected from the group consisting of 1,8-cineole; 1-methyl-1,4-cyclohexadiene; and (+)-α-methylene-α-fenchocamphorone.

7. The method of claim 6, further comprising isolating the at least one compound from the culturing media or from vapor in the container.

8. A kit for making at least one compound selected from the group consisting of 1,8-cineole; 1-methyl-1,4-cyclohexadiene; and (+)-α-methylene-60-fenchocamphorone comprising at least one fungus that is an isolate selected from the group consisting of Co27-5 (deposited as NRRL 50500); CI-4 (deposited as NRRL 50501); Ti-13 (deposited as NRRL 50502); and Ec-38 (deposited as NRRL 50503), and instructions for growing the fungus for production of the at least one compound, on or within a culturing media in a container under conditions sufficient for producing the at least one compound.

9. The kit of claim 8, wherein the fungus is serially propagated.

10. The kit of claim 8, further comprising a high-starch substrate for culturing the fungus in or on.

11. The kit of claim 8, further comprising ingredients for a liquid medium for culturing the fungus in.

12. The kit of claim 8, further comprising ingredients for a solid medium for culturing the fungus on.

* * * * *